United States Patent
Stegmann

(10) Patent No.: US 9,816,946 B2
(45) Date of Patent: Nov. 14, 2017

(54) METHODS AND APPARATUS FOR THE PREPARATION OF MICROSCOPY SAMPLES BY USING PULSED LIGHT

(71) Applicant: Heiko Stegmann, Dresden (DE)

(72) Inventor: Heiko Stegmann, Dresden (DE)

(73) Assignee: Carl Zeiss Microscopy GmbH, Jena (DE)

( * ) Notice: Subject to any disclaimer, the term of this patent is extended or adjusted under 35 U.S.C. 154(b) by 1165 days.

(21) Appl. No.: 13/765,022

(22) Filed: Feb. 12, 2013

(65) Prior Publication Data

US 2013/0213945 A1    Aug. 22, 2013

(30) Foreign Application Priority Data

Feb. 17, 2012    (DE) ......................... 10 2012 202 519

(51) Int. Cl.
| | |
|---|---|
| *G01N 23/04* | (2006.01) |
| *G01N 1/28* | (2006.01) |
| *G01N 1/44* | (2006.01) |
| *G01N 1/04* | (2006.01) |

(52) U.S. Cl.
CPC ............ *G01N 23/04* (2013.01); *G01N 1/286* (2013.01); *G01N 2001/045* (2013.01); *G01N 2001/2886* (2013.01)

(58) Field of Classification Search
CPC .. G01N 1/286; G01N 23/04; G01N 2001/045; G01N 2001/2886
See application file for complete search history.

(56) References Cited

U.S. PATENT DOCUMENTS

| | | | | |
|---|---|---|---|---|
| 4,918,611 A | * | 4/1990 | Shyu ................. | G05B 19/4205 219/121.67 |
| 5,656,186 A | * | 8/1997 | Mourou ................ | B23K 26/40 219/121.69 |

(Continued)

FOREIGN PATENT DOCUMENTS

| | | |
|---|---|---|
| CN | 1151925 | 6/1997 |
| CN | 101776882 A | 7/2010 |

(Continued)

OTHER PUBLICATIONS

Translation of Japan Patent No. 10-006,052, Nov. 2016.*

(Continued)

*Primary Examiner* — Geoffrey S Evans
(74) *Attorney, Agent, or Firm* — Fish & Richardson P.C.

(57) ABSTRACT

Methods and apparatus are disclosed for the preparation of microscopic samples using light pulses. Material volumes greater than 100 μm³ are removed. The methods include inspecting an object with a scanning electron microscope (SEM) or a focused ion beam (FIB). The inspection includes recording an image of the object. The methods also includes delineating within the object a region to be investigated, and delineating a laser-machining path based on the image of the object so that a sample can be prepared out of the object. The methods further include using laser-machining along the delineated laser-machining path to remove a volume that is to be ablated, and inspecting the object with the scanning electron microscope (SEM) or a focused ion beam (FIB).

21 Claims, 5 Drawing Sheets

(56) References Cited

U.S. PATENT DOCUMENTS

| | | | |
|---|---|---|---|
| 6,407,373 B1* | 6/2002 | Dotan | G01N 21/9501 250/201.3 |
| 7,414,252 B2* | 8/2008 | Moore | B82Y 15/00 250/492.21 |
| 7,442,924 B2 | 10/2008 | Giannuzzi et al. | |
| 7,842,920 B2* | 11/2010 | Lundquist | G01Q 30/20 250/306 |
| 8,071,960 B2 | 12/2011 | Hoeche | |
| 8,115,180 B2 | 2/2012 | Doemer et al. | |
| 8,350,227 B2 | 1/2013 | Doemer et al. | |
| 2004/0016888 A1* | 1/2004 | Haraguchi | H01J 37/28 250/440.11 |
| 2004/0245466 A1 | 12/2004 | Robinson et al. | |
| 2006/0022148 A1 | 2/2006 | Fischione et al. | |
| 2006/0226359 A1* | 10/2006 | Principe | G01N 1/32 250/310 |
| 2007/0272854 A1* | 11/2007 | Agorio | G01N 1/286 250/304 |
| 2008/0296498 A1* | 12/2008 | Hong | H01J 37/3056 250/311 |
| 2009/0057268 A1* | 3/2009 | Aviel | B41C 1/05 216/65 |
| 2010/0051828 A1* | 3/2010 | Doemer | H01J 37/20 250/492.1 |
| 2010/0054565 A1* | 3/2010 | Quinto | G01N 23/046 382/131 |
| 2010/0127190 A1 | 5/2010 | Straw et al. | |
| 2010/0148064 A1* | 6/2010 | Harrach | H01J 37/244 250/307 |
| 2010/0158392 A1* | 6/2010 | Adams | G01N 23/203 382/218 |
| 2010/0276405 A1* | 11/2010 | Cho | H01L 23/5258 219/121.72 |
| 2011/0163068 A1* | 7/2011 | Utlaut | G03F 1/84 216/66 |
| 2011/0198326 A1 | 8/2011 | Doemer | |
| 2011/0248164 A1 | 10/2011 | Straw et al. | |
| 2012/0132799 A1* | 5/2012 | Takahashi | H01J 49/0004 250/288 |
| 2013/0143412 A1* | 6/2013 | Moriarty | G01N 1/286 438/759 |
| 2014/0131195 A1* | 5/2014 | Bruland | H01J 37/228 204/192.34 |

FOREIGN PATENT DOCUMENTS

| | | |
|---|---|---|
| CN | 102229023 | 11/2011 |
| DE | 102008045336 | 3/2010 |
| DE | 102008052006.3 | 4/2010 |
| DE | 102010008296 | 8/2010 |
| EP | 2359977 | 8/2011 |
| JP | 10-006052 A * | 1/1998 |
| JP | 2008-18547 A * | 1/2008 |

OTHER PUBLICATIONS

German Office Action, with English translation, issued in DE 10 2012 202 519.7 dated Jun. 17, 2013.
Chinese Office Action, with English translation thereof for corresponding CN Appln. No. 201310158953.6, 22 pages, dated May 24, 2016.
Chinese Office Action with English translation thereof for corresponding CN Appln. No. 201310158953.6, dated Dec. 7, 2016, 25 pages.
Chinese Office Action and Search Report, with translation thereof, for corresponding Appl No. 201310158953.6, dated Jul. 13, 2017.

* cited by examiner

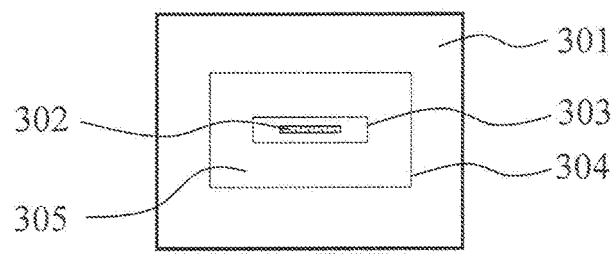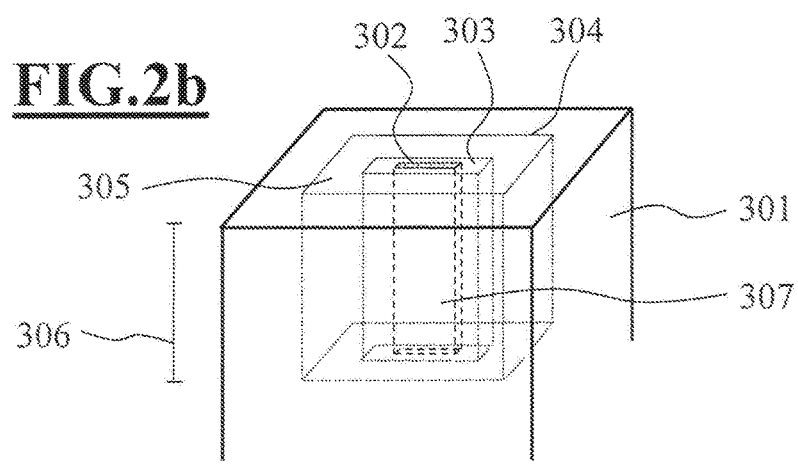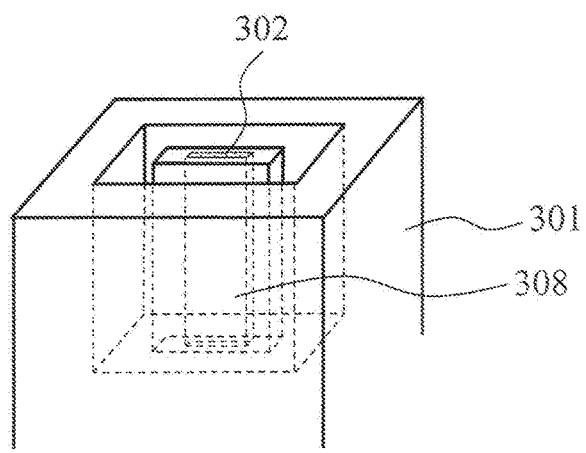

FIG.3
FIG.3a
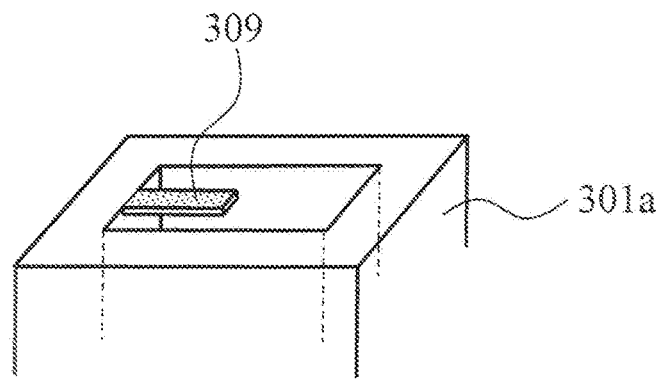
FIG.3b
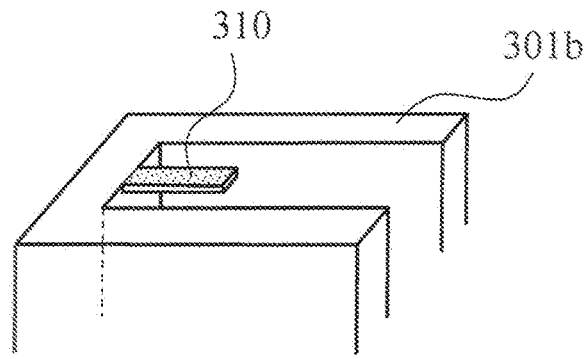
FIG.3c
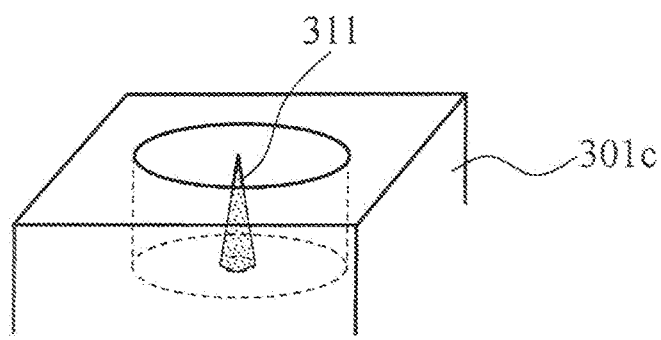
FIG.3d
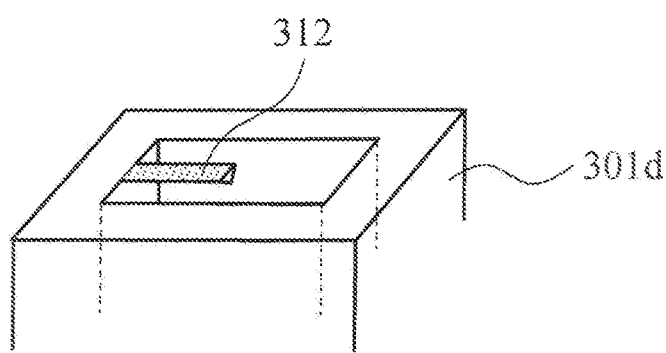

METHODS AND APPARATUS FOR THE PREPARATION OF MICROSCOPY SAMPLES BY USING PULSED LIGHT

CROSS-REFERENCE TO RELATED APPLICATION

This application claims benefit under 35 U.S.C. §119 of German patent application DE 102012202519.7, filed Feb. 17, 2012, the entire contents of which are incorporated herein by reference.

FIELD

The disclosure concerns methods and apparatus for preparing microscopy samples of different kinds by using pulsed light.

BACKGROUND

The application of contemporary microscopy methods such as transmission electron microscopy, nanotomography, or the investigation of micromechanics-related aspects of materials often involves the preparation of three-dimensional samples with complex geometries. This can involve the removal of material volumes of a few tenths of a cubic micrometer ($\mu m^3$) up to several tens of cubic millimeters ($mm^3$). Given that in most cases only a specific portion of the object is of interest as a sample, one generally cannot arbitrarily select any region of the object for preparation as a sample. Rather, it is desirable to prepare a defined target structure out of the object in order to obtain the desired sample.

In the practice of transmission electron microscopy, so-called TEM lamellae are used which are transmittent to electrons. The length and width of the TEM lamellae are in most cases of the order of several microns ($\mu m$); their thickness in most cases is less than one hundred nanometers (nm). To ensure that TEM lamellae contain the desired targeted structure, they normally are prepared out of the full object material.

In nanotomography methods, the microscopy sample is cut away layer by layer, recording an image of each layer. The layer images obtained in this manner are then assembled into a three-dimensional reconstruction of the sample structure. In FIB/SEM tomography, the layers are removed via a focused ion beam (FIB), while the images of the layers are recorded with a scanning electron microscope (SEM). In addition, the elementary composition of the sample can be investigated via energy-dispersive X-ray spectroscopy (EDS), wherein the element-specific X-ray spectrum is analyzed which is emitted by the sample material in response to the incident electron beam.

As a further possibility, the samples can be investigated using wavelength-dispersive X-ray spectroscopy (WDS).

In samples that contain crystalline structures, the technique of electron backscatter diffraction (EBSD) can be used to investigate the distribution of the crystal orientations based on the back-scattered electrons. As a general principle for tomography samples, especially if the same sample is also to be used to perform EDS- or WDS analyses, the target volume first is set free within a larger material space in order to avoid unwanted obscuration- and/or redeposition effects. In the case of FIB/SEM tomography, samples are prepared in the shape of rectangular blocks which remain connected to the object along one of the shorter side surfaces or, alternatively, along one of the short surfaces and also at the base surface. Similar block-shaped samples are used for EBSD investigations. In this case, however, all of the object material on one side is removed, so that the sample block stands out into free space. For investigations with high-resolution X-ray tomography or synchrotron radiation tomography, needle-shaped samples are used. A needle-shaped sample in essence has the shape of a cone with a base diameter that is small in proportion to its height and with a long, pointed apex. While the needle-shaped sample rotates about its longitudinal axis, a plurality of images are recorded using conventional X-rays or synchrotron radiation and using suitable detectors, whereupon the recorded images can be assembled into a three-dimensional representation of the sample.

For an in-situ investigation of micromechanical material properties, one uses samples of specific geometric shapes, for example rod-shaped samples for use as bending beams, which have been prepared out of the full sample material. Cantilever beams, which are rigidly held at one end and free at the other, are for example well suited for the investigation of the elastic properties of a material. In experiments of this kind, the bending beam which measures in most cases only a few hundred microns in length is subjected to a controlled deformation which is simultaneously observed with the scanning electron microscope (SEM). With rod-shaped samples, the behavior of a material under tension or compression can be investigated with the scanning electron microscope by observing changes in the microscopic material structure under tensile or compressive loads.

Systems are known in which an electron microscope is used to investigate the sample and where the radiation beam generated by the electron microscope is also used to activate a process gas which is delivered to the sample, so that the activated process gas will modify the sample as material is removed or separated from the sample.

Also known are systems that include an electron microscope and an ion beam column whose radiation beams can be aimed simultaneously or alternatively at a location of a sample that is to be modified. Here, the ion beam serves to modify the sample while the progress of this process can be observed with the electron microscope. Additionally, it is possible in such a system to inject process gas in order to modify the sample through the process gas which is activated by the electron- or ion beam. In the in-situ lift-out method, the sample that is to be prepared is cut free by the focused ion beam and subsequently transferred to a suitable sample carrier by a micromanipulator.

Although sample preparation with an electron beam and/or an ion beam and/or an activated process gas can be performed with a high degree of precision, such systems have the disadvantage that this kind of preparation is very slow and not always successful. In a process where a large sample volume is to be removed, this procedure will take a relatively large amount of time. Also, especially with the in-situ lift-out method the operator desirably has experience and experimental skill.

It is also known that laser-machining systems, especially of the type working with solid state lasers, can be used for the cutting, removing, drilling, welding or soldering of materials. The state of the art further includes systems in which a laser beam serves to remove material from a sample that is normally of a size of at most a few millimeters. To perform this process, a laser beam of sufficient radiation energy, i.e. photon energy, is aimed at predetermined target locations of the object by way of a sensor device or scanning device. This is accomplished by setting the scanner sweep of the scanning device in accordance with coordinates of the target locations in a coordinate system of the scanning device.

Also known are machining systems that include a particle beam column to generate a targeted particle beam and a laser system to generate a targeted laser beam. The particle beam column can include an electron beam column and an ion beam column, wherein these particle beam columns can also be configured for example as an electron microscope or an ion microscope insofar as they include a secondary particle detector. The secondary particle detector can for example be an electron detector or an ion detector.

Furthermore, a laser-machining system has been described in which an object can be machined with a comparatively high level of precision, wherein a changeover of the object in process is possible between a machining operation in the laser-machining system and a machining operation and/or inspection in a further machining and/or inspection system such as for example a scanning electron microscope. To meet this purpose, an object holder has been proposed which carries markings that allow the accurate, and thus reproducible, positioning of the targeted sample location.

The following references may be considered relevant: DE 10 2008 045 336; U.S. Pat. No. 7,442,924; and DE 10 2010 008 296.

SUMMARY

The disclosure proposes methods and apparatus whereby material can be removed in a relatively short time in order to prepare a sample.

The method according to the present disclosure concerns the preparation of samples using light pulses, wherein volumes greater than 100 $\mu m^3$ are removed, and entails the following steps. First, an object is inspected with a scanning electron microscope (SEM) or a focused ion beam (FIB), whereby an image of the object is obtained. Next, based on the image, the area to be investigated within the object is delineated in such a way that the desired sample can be prepared out of the material of the object. Along the laser-machining path delineated in this manner, the object material volume that is to be taken off is removed, so that the desired target structure remains in place in the sample. Subsequently, the sample is inspected with a scanning electron microscope (SEM) or a focused ion beam (FIB).

A method according to the disclosure is suited for example for the purpose of preparing TEM lamellae. TEM lamellae are samples that can be investigated with transmission electron microscopes (TEM), as the TEM lamellae are transmittent to electrons. This means that electrons of an electron beam generated in the transmission electron microscope are able to pass through the sample material of the TEM lamella. Normally, TEM lamellae are shaped in essence as a flat rectangular slab, wherein the sides of the base surface are in most cases several microns long, while the height of the slab in most cases measures only a few nanometers up to several tens of nanometers, so that the TEM lamella is permeable to electrons.

In the method according to the disclosure the object to be prepared, which is located in a processing chamber, is first visually examined and an image of the object is made. In this way, object portions that are of interest, i.e. the target structures that are to be contained subsequently in the TEM lamella, can be identified. Accordingly, the object zone is delineated, out of which the TEM lamella is to be prepared in a following phase of the process. Normally, one of the side surfaces of the slab-shaped TEM lamella that is to be prepared lies on the outside of the object, visible from above. The object zone to be prepared is delineated by superimposing a boundary demarcation, for example a rectangle, on the image of the object using an operating software program. The superimposed boundary demarcation represents the outline of a preliminary stage of the TEM lamella in top view. The demarcated area of the preliminary stage of the TEM lamella is usually bigger than the surface of the TEM lamella, since later on material will be removed from the preliminary stage of the TEM lamella until the latter has attained the desired final dimensions.

Next, a second boundary demarcation which totally encloses the first boundary demarcation is added by the operating software program. In other words, the second boundary demarcation is larger than the first boundary demarcation, and the area enclosed by the first boundary demarcation lies entirely within the area of the second boundary demarcation. The second boundary demarcation can for example be a rectangle. The area within the second boundary demarcation minus the part that lies within the first boundary demarcation defines the zone of the object where material is to be removed. The working path of the laser beam can be defined with the software program, namely by determining the movement pattern by which the laser beam is to be guided over the object surface to be machined, i.e. for example in parallel rows or in a circular path. The size of the second boundary demarcation can be freely selected, depending on how much material is to be removed. Normally, the second boundary demarcation is of similar or equal shape as the first boundary demarcation which delineates the preliminary stage of the TEM lamella.

Depending on the desired shape of the sample, the superimposed boundary demarcation may have any other geometric shape. This depends on the shape of the base surface of the three-dimensional sample body that is to be prepared. In order to obtain for example a cylindrical or cone-shaped sample, a circular boundary demarcation is superimposed on the object image. The positions of the superimposed boundary demarcations can be converted into coordinate values and stored in memory, so that the demarcated zones can later be found again. In a special embodiment, the boundary demarcations set by the user can be stored and later retrieved for further use. In another embodiment, a multitude of different boundary demarcations is filed in the software program, so that the user can make a selection from a collection of preprogrammed boundary demarcations. Both embodiments are designed to allow and to facilitate the standardization and automation of the sample preparation.

According to the present disclosure, in a next-following step the sample volume that is to be cleared away is removed by laser-machining along the defined laser-machining path. That is to say, that a volume of material, which is 100 $\mu m^3$ or greater is ablated using light pulses. The removed volume is converted into a cloud of material that can be cleared away by evacuating the processing chamber with a pump. In one embodiment of the disclosure, a pulsed laser is employed with preference, for example a pulsed solid state laser. Solid state lasers normally consist of crystals or glasses that are doped with optically active ions, examples of which are YAG (yttrium aluminum garnet) lasers, or Nd:YLF (neodymium-doped yttrium lithium fluoride) lasers, which differ from each other in the wavelength of the emitted monochromatic laser light.

Alternatively, it is also conceivable to use other kinds of lasers for the laser-machining, for example gas lasers, excimer lasers or other types of lasers that are suitable for the machining of materials. Since laser light is coherent and directionally aligned, the laser light bundle can be sent over long distances and can be strongly focused. As a result, very high power densities (power per unit of area) can be generated on the surface of the object that is to be machined. Lasers operating in pulse mode, which are characterized by the parameters of power (energy per unit of time), pulse duration and pulse frequency, are the preferred choice for the machining of materials.

A special embodiment of the present disclosure includes a UV-pulse laser, preferably with a wavelength of 355 mm and a mean pulse duration of 10 ns, wherein the pulse duration can range from 5 ns to 17 ns. Depending on the kind of material that is to be removed, it is possible to use lasers of different wavelengths, i.e. with wavelengths in the range of visible light, and also with wavelengths in the infrared range or in the higher-energy ultraviolet (UV) range of the spectrum.

The parameters of pulse duration, pulse power, pulse frequency and wavelength should be suitably adapted to the kind of material that is to be ablated. According to a special embodiment, a laser that is used with preference for the ablation of metals has a pulse duration of only a few picoseconds (ps) or femtoseconds (fs), not exceeding 20 ps. In a further embodiment an $Nd:VO_4$ solid state laser is employed for example for the machining of silicon-containing materials such as semiconductor materials or encapsulated semiconductor components.

The depth to which the material is removed can be set by way of the total time during which the laser light is applied as well as by varying the pulse frequency and/or pulse energy. Each time a laser pulse arrives on the object to be machined, object material is subjected to a phase transition into the gas- or liquid phase, or material is blasted off in the form of particles, so that as an overall effect a volume of material is cleared away from the object. The pulse frequency of the laser pulse should be selected so that the cloud of material which occurs in the removal process is no longer present near the object when the next laser pulse hits the object. The disappearance of the cloud of material can be accelerated by evacuating the processing chamber with a pump.

The laser-machining process can be performed under vacuum conditions or in a nitrogen-oxygen atmosphere. Further, in a special embodiment the process chamber can be filled with a suitable process gas so that a chemical reaction designed to accelerate the removal of material will take place between the object material and the process gas. In the selection of a suitable process gas, the conditions that are present for the reaction as well as the chemical nature of the object material are taken into account.

In another special embodiment, a suitable gas is directed in a targeted manner and under pressure, e.g. 6 bar above atmospheric pressure, using a gas injection system with a jet nozzle at the object surface from which material is to be removed. Due to the mechanical action of the gas jet, the cloud of material taken off by the laser is removed from the machining location, so that the removal process is accelerated. Gases that are suitable for this purpose include for example air, nitrogen, or inert gases such as argon.

Another factor that enters into the optimization of the laser-machining parameters is the slope of the leading pulse flank. In order to minimize heat damage to the sample, the pulse frequency should be selected sufficiently high and the pulse duration should be selected sufficiently short. In order to totally eliminate the risk of heat damage from laser action, a final layer of about 10 to 15 µm of surface material directly surrounding the target structure can be removed with the focused ion beam instead of the laser.

According to one embodiment, the object can be observed with a scanning electron microscope and/or a focused ion beam during the laser-machining. According to another embodiment, likewise mentioned here as an example, the object is not observed during the laser-machining.

According to one embodiment, after the laser-machining has been completed the object in its prepared form can be inspected with a scanning electron microscope (SEM) and/or a focused ion beam (FIB).

According to one embodiment, after the volume to be removed has been cleared away, the surfaces of the object that were obtained as a result of the laser-machining are finished with the focused ion beam. While this finishing process takes place, it can be observed with the scanning electron microscope.

According to one embodiment, a first processing chamber is the sample chamber of a scanning electron microscope. In a further embodiment, the first processing chamber is the sample chamber of a dual beam microscope which includes an electron beam column and, arranged at an angle relative to the latter, an ion beam column, so that an object that is present in the sample chamber can be selectively irradiated with an electron beam and/or an ion beam.

According to one embodiment, a first processing chamber is connected to a scanning electron microscope and/or ion microscope. A second processing chamber is connected to a laser-machining system. The object can be transferred from the first processing chamber into the second processing chamber and vice versa.

In a special embodiment, the object to be machined is attached to an object holder. This object holder is suitably designed to hold the object in the first processing chamber as well as in the second processing chamber. The object holder further allows the object to be transferred from the first processing chamber into the second processing chamber as well as from the second processing chamber into the first processing chamber. The machining system according to the disclosure is designed so that the coordinates of the selected boundary demarcations that have been superimposed on the SEM image of the object can be referenced to the object carrier and stored in memory. This makes it possible to position the object again by recalling the stored coordinates after the object holder and object have been transferred into the laser-machining chamber. The machining system further includes a controller consisting of a computer unit and an operating software program. Based on the known coordinates, the controller can guide the laser beam using deflection mirrors along a predetermined laser-machining path, so that the laser beam arrives and performs its machining function precisely in the desired machining area. As the laser beam is guided by the controller only through the predefined machining area, observation of the sample during the laser-machining process is not required. Nevertheless, the sample can be observed during the laser operation with a suitable detector or camera.

A method according to the disclosure is designed to produce samples for nanotomography scanning. In order to avoid obscuration and redeposition effects in the tomography process, the area around the target volume is cleared away with a wide reach. The method according to the disclosure includes the capability to produce samples of different shapes. For example, free-standing slab-shaped samples can be produced which remain connected to the object only along one of the shorter side surfaces. Samples of this shape are used for FIB/SEM tomography. In order to arrive at the slab-shaped sample, one starts by clearing away the material around the contours of a rectangular block. Next, the object is tipped over, so that using the laser the material at the underside of the block can be removed, until five sides of the sample block are set free and the sample block remains connected to the object material only along one of the short side surfaces. Alternatively, the first mentioned undercut by which the material at the underside of the block is removed can be omitted, so that the sample remains connected to the object material not only along one of the short side surfaces but also at the base surface (i.e. one of the two largest surfaces) of the block.

Similar block-shaped samples are used for electron backscatter diffraction (EBSD) investigations. However, in this case all of the object material on one side is cleared away, so that the sample block is freely accessible on that side.

With a method according to the disclosure, it is also possible to produce needle-shaped samples. To accomplish this, the first boundary demarcation is laid out in circular shape, so that after stripping away the desired volume, a needle-shaped sample body remains standing. The needle-shaped sample can be separated from the object by making an undercut. Needle-shaped samples with a diameter up to 60 μm are used for investigations with energy-dispersive X-ray spectroscopy (EDS) or wavelength-dispersive X-ray spectroscopy (WDS). Needle-shaped samples with a diameter up to 60 μm are also needed for high-resolution X-ray tomography with conventional X-ray sources. Needle-shaped samples with a diameter up to 200 μm are used for tomography scans with synchrotron radiation.

In the field of medicine, tomographic methods are used for example in osteoporosis research. For this purpose, needle-shaped bone samples are tomographically investigated. The preparation of samples with lasers using a pulse duration of femtoseconds (fs) or picoseconds (ps) has the advantageous side effect that samples which contain water—such as for example bone samples—do not have to be completely dehydrated prior to the machining with the laser.

Another method according to the disclosure is designed to produce samples for in-situ investigation of micromechanical material properties. Samples used for this purpose are normally rod-shaped or configured as free-standing bending beams.

In another method according to the disclosure, a sample lift-out is performed with a micromanipulator. This means that the prepared sample is separated from the object material and transferred to a suitable sample holder with a micromanipulator. The sample holder with the sample can then be taken out of the apparatus.

In another method according to the disclosure the prepared sample is separated from the object by making an undercut. Normally, to accomplish this, the target volume is cleared away to the point where the sample remains connected to the object only in a spatially limited connection zone. Then, the object can be tipped over, so that the connection zone that is to be cut apart can be reached by the laser beam. With a laser cut through the connection zone, the sample is separated from the object. Alternatively, the cut can also be performed with a focused ion beam.

The methods according to the disclosure have the advantage that material volumes of more than 100 μm$^3$ can be cleared away in a few minutes. In the method of the disclosure, the process of laser-machining can be employed in particular if sample volumes of more than 100 μm$^3$ have to be removed, while object zones having a smaller volume of material (i.e. less than 100 μm$^3$) to be ablated can be machined with a focused ion beam or electron beam.

According to an embodiment of the present disclosure, ablation of volumes to be removed, is performed using a laser beam, when the volume to be ablated measures 100 μm$^3$ or more, whereas ablation of volumes to be ablated is performed using a focused particle beam, when the volume to be ablated is less than 100 μm$^3$. In other words: According to the disclosure it is possible to combine coarse machining done with pulsed light pulses and fine machining done with a particle beam.

Coarse machining means that light pulses clear away a volume of material, which is at minimum 100 μm$^3$. Normally, the volume to be removed is vaporized by the impact of the laser beam or blasted off in the form of particles, so that the ablated material can be pumped away from the processing chamber.

Fine machining means that a focused particle beam, for example an ion beam or an electron beam, removes a volume of material less than 100 μm$^3$. In case of fine machining using an ion beam, removal of the material can be done by sputtering or sputtering in combination with additional injection of a suitable process gas. In case of removal of material using an electron beam, it is advantageous, if the ablation of material is done by the interaction of the electron beam together with a suitable process gas, in a way that an electron beam-induced gas-chemical process is maintained. As well the material removed by fine machining is cleared away from the processing chamber by pumping.

Thus, methods according to the disclosure are suitable for preparing microscopic samples of different kinds within a short time. It is a further advantage of the disclosure that the implantation of ions is avoided, which occurs when large sample volumes are removed using a focused ion beam. Likewise avoided are the risks of mechanical damage to the sample or of chemical changes which can occur in conventional methods as a result of mechanical operations or as a result of interaction with process gases.

It has appeared to be advantageous, that the object, the sample is to be prepared from, is held on a specimen stage in the processing chamber. According to the disclosure, a volume of material equal to or greater than 100 μm$^3$ is removed and discarded, whereas the detail of interest, which has been prepared as the sample, is still connected to the object. Thus, the object together with the prepared sample can be inspected easily with a scanning electron microscope and/or a focused ion beam.

An apparatus according to the present disclosure is suitable for the preparation of samples using light pulses involving the removal of sample volumes larger than 100 μm$^3$. The apparatus includes an ion microscope serving to generate a focused ion beam (FIB) and/or a scanning electron microscope and further includes a laser system to perform the laser-machining. The apparatus according to the disclosure is suited to take an image of the object using the focused ion beam and/or the scanning electron microscope, based on which a laser-machining path can be delineated. The laser system of the apparatus is configured in such a way that the sample can be prepared out of the sample material along the laser-machining path that has been delineated. The prepared sample can be inspected with the scanning electron microscope (SEM) and/or the focused ion beam (FIB) of the apparatus.

According to one embodiment, a first processing chamber is the sample chamber of a scanning electron microscope. In a further embodiment, the first processing chamber is the sample chamber of a dual beam microscope that includes a scanning electron microscope as well as an ion beam column, so that an object that is present in the sample chamber can be irradiated selectively with an electron beam and/or an ion beam.

According to one embodiment of the apparatus of the disclosure, a first processing chamber is part of a scanning electron microscope or of a dual beam microscope, whereas a second processing chamber is connected to a laser system serving to perform the laser-machining. The apparatus is configured so that the object can be transferred from the first processing chamber to the second processing chamber. The object can further be transferred from the second processing chamber to the first processing chamber.

According to an exemplary embodiment, the laser system for the laser-machining includes a UV pulse laser operating for example with a wavelength of 355 nm and a mean pulse duration of 10 ns.

The apparatus according to a special embodiment includes a micromanipulator serving to perform a lift-out of the sample and also includes a suitable sample carrier. In the lift-out operation, the prepared sample is separated from the object material and transferred to the sample carrier using the micromanipulator. The sample carrier and the apparatus are designed in such a way that the sample carrier can be taken out of the apparatus.

EXAMPLES OF EMBODIMENTS

Examples of embodiments of the disclosure will be explained in the following with the help of drawings, in which:

FIG. 2 shows an example for the preparation of a TEM lamella, wherein:

FIG. 2a represents a top view of the object;

FIG. 2b schematically illustrates the boundary demarcation for the delineation of the laser-machining path; and FIG. 2c schematically illustrates the preliminary stage of the TEM lamella after clearing away the desired volume of material by laser-machining;

FIG. 3 illustrates different sample shapes, wherein:

FIG. 3a shows an FIB/TEM tomography sample;

FIG. 3b shows an EBSD sample;

FIG. 3c shows a sample for X-ray or synchrotron tomography; and

FIG. 3d shows a bending beam for a material investigation.

Figure 4:
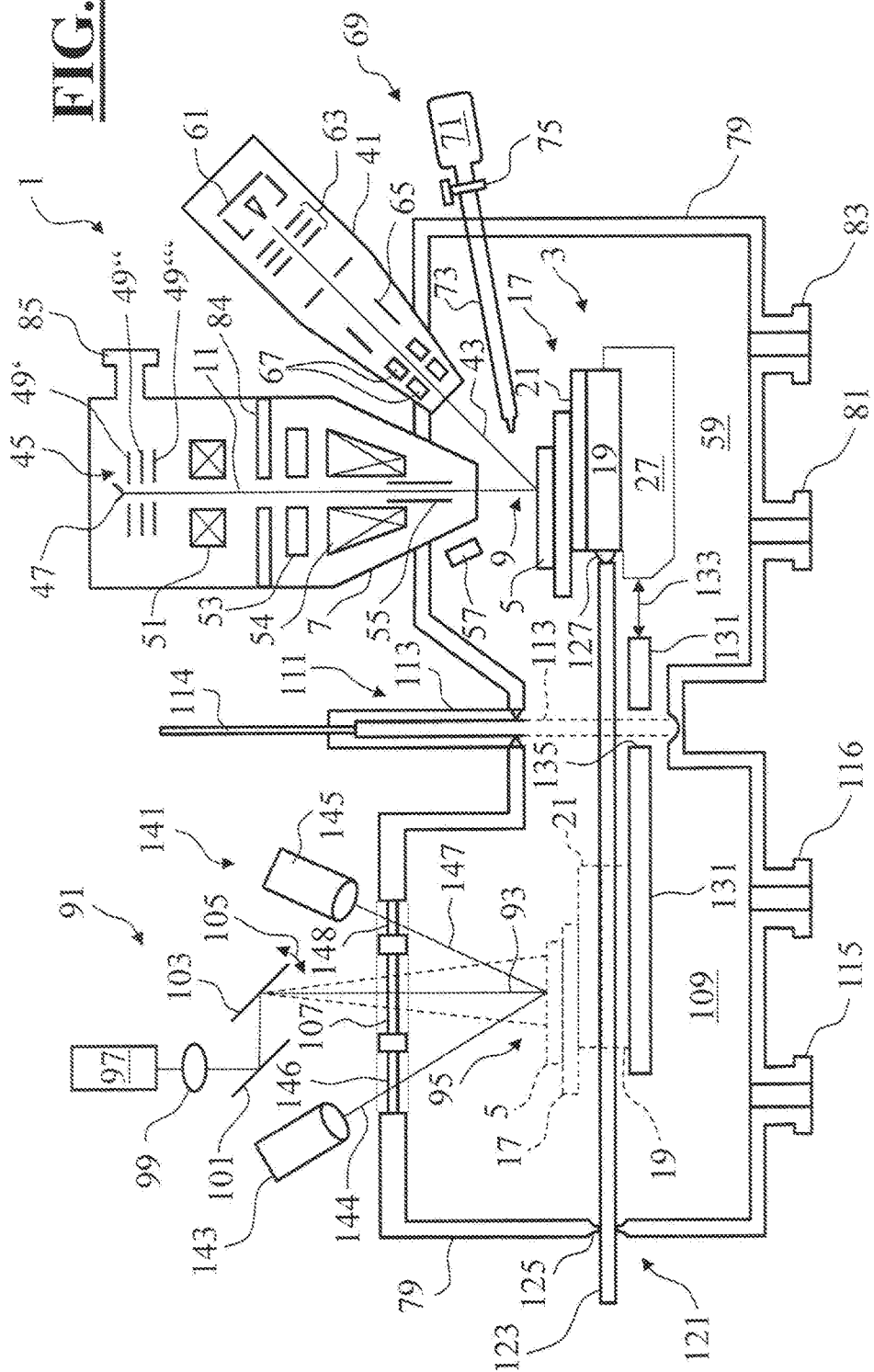

FIG. 4 schematically illustrates an exemplary embodiment of the apparatus according to the disclosure.

Figure 5:
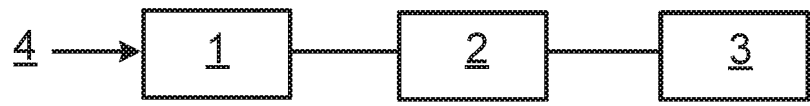

FIG. 5 schematically illustrates a system that includes a machining system, a controller and a memory.

DETAILED DESCRIPTION

In the following, embodiments of the disclosure will be explained in connection with the drawings. Components that are analogous to each other in regard to their structure and function are identified by reference symbols that have the same numerals but are distinguished by adding different letters. For the explanation of the components, reference is in each case also made to the respectively preceding and following parts of the description.

Figure 1:
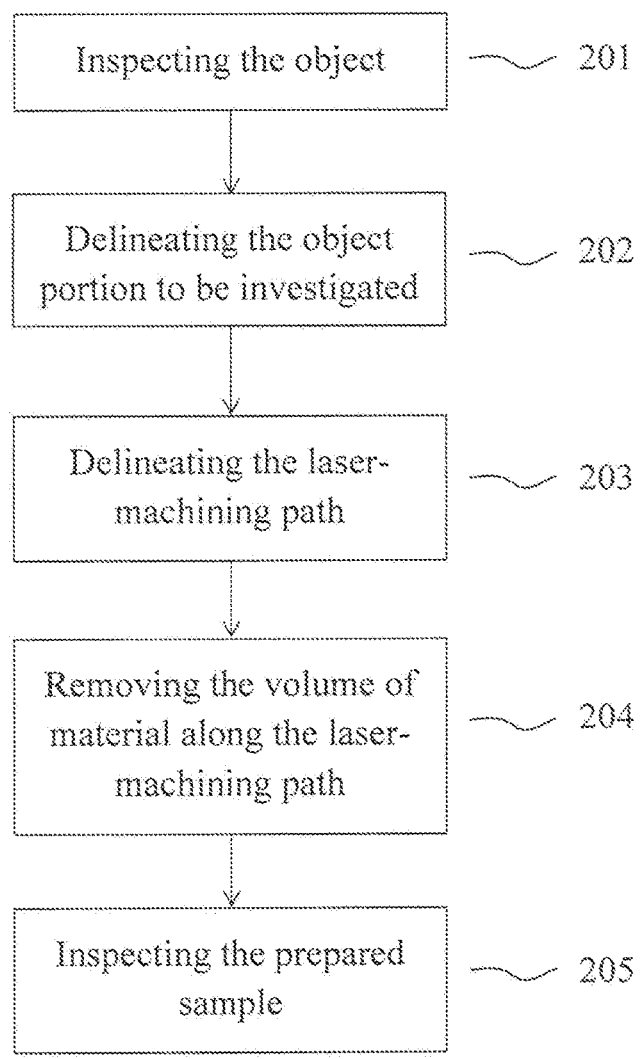
FIG. 1 represents a flowchart diagram of a method according to the disclosure.

FIG. 1 represents a flowchart of a method according to the disclosure. The object out of which the sample is to be prepared is located in a processing chamber of a processing system according to the disclosure. In step 201 the object is inspected. The inspection can be performed with an electron microscope or a focused ion beam, or with a combination of electron microscope and focused ion beam. In any case, an image is recorded which can be stored in memory for possible later use. In step 202, the object portion to be investigated is delineated on the basis of the image that was recorded in step 201. Normally, only certain areas of the object are of interest, since a specifically defined target structure has to be contained within the sample that is to be prepared. The area that is to be investigated is selected accordingly and demarcated in the image using a software program (see FIGS. 2a and 2b). In step 203, a second boundary demarcation is superimposed on the image. The second boundary demarcation is larger than the first boundary demarcation, so that the area of the first boundary demarcation lies completely inside the area of the second boundary demarcation. The area that lies within the second boundary demarcation, but without the part that lies within the first boundary demarcation, defines the zone of the object that is to be cleared of material through laser-machining. Using the software program, the laser-machining path can be delineated along which the laser beam is to be guided over the object zone that is to be machined. In step 204, the material is cleared away along the laser-machining path. The removal of material occurs by way of laser ablation. In step 205, the prepared sample is inspected. If desired, a finishing process may be added (for example polishing) with a focused ion beam or with a process-gas-assisted electron etching process. This is advisable in particular if peripheral parts of the finished sample that had been damaged by the laser beam are reworked, i.e. removed, by the subsequent finishing process.

FIGS. 2a to 2c illustrate as an example a sequence of steps in the preparation of a TEM lamella. FIG. 2a shows the object 301 in top view, and FIG. 2b shows the object 301 in a perspective view. An image of the object 301 is recorded which shows the object in top view. In this image, the target structure 302 which is to be contained later in the sample can be identified. Using an operating software program, a first boundary demarcation 303, representing a preliminary stage of the TEM lamella, can be overlaid on the image of the object 301. The preliminary stage of the TEM lamella is larger than the target structure 302 since later on, material will continue to be removed from the preliminary stage of the TEM lamella until the latter has attained the desired final dimensions. Likewise using the software program, a second boundary demarcation 304 which contains within itself the first boundary demarcation is inserted into the image. The area of the second boundary demarcation 304 minus the part that lies within the first boundary demarcation 303 represents the base area of the body of material 305 that is to be cleared away and thus defines the area in which the laser-machining path lies. The exact map of the laser-machining path is determined using the software program. Depending on the narrowest possible focus of the laser beam, there is normally a minimum width for the area between the boundary demarcations. The software program can prescribe the minimum width in the superimposed image. In an alternative embodiment the software program can advise, in response to a user-entered machining width for the sample in process, whether the desired machining width can be processed with the laser beam or with a focused particle beam.

The volume 307 to be removed, which is defined by the base area 305 and the ablation depth 306, is cleared away with the laser along the laser-machining path. The ablation depth 306 is normally determined by the total amount of machining time during which the laser light is applied. In one embodiment, the user can select the desired ablation depth 306 in the software program, as the software contains a data file in which the ablation rates are tabulated as a function of the material to be processed and the size of the demarcated machining area. Based on the stored table data, the controller can determine the total machining time for a desired ablation depth 306. Another embodiment has the additional capability that the user himself can determine further ablation rates for any desired materials and store them in a data file in the software program for later use.

FIG. 2c shows the machined object 301 wherein the volume that had to be removed has been completely cleared away, so that the preliminary stage of the TEM lamella 308 is left as a free-standing structure.

FIG. 3 shows examples of different types of samples that can be produced with the method according to the disclosure. FIG. 3a illustrates a slab-shaped FIB/SEM tomography sample 309 which has been formed out of the material of an object 301a. FIG. 3b shows an EBSD sample 310 which is suitable for EBSD analyses. The sample has been formed in the shape of a slab out of the material of an object 301b. Unlike the FIB/SEM tomography sample 309, the material on one side of the object 301b has been completely removed, so that the EBSD sample 310 is freely accessible from that side. FIG. 3c show an X-ray/synchrotron tomography sample 311 which is of needle-shaped configuration and is suitable for X-ray tomography and/or synchrotron tomography. FIG. 3d shows a bending beam 312 for a micromechanical material investigation.

FIG. 4 schematically represents an example of an embodiment of the apparatus for the preparation of samples in accordance with the disclosure. Illustrated is a machining system 1. The machining system 1 includes two particle beam columns, namely the electron beam column 7 to generate the electron beam 11, and an ion beam column 41 to generate an ion beam 43 which, like the electron beam 11, is aimed at the inspection target location 9. The electron beam column 7 includes an electron source 45 with a cathode 47, a suppressor electrode 49', an extractor electrode 49", and an anode 49''', a condenser lens system 51 to generate the beam 11, a secondary electron detector 53 which may be arranged for example within the column 7, and an objective lens 54 to focus the electron beam 11 on the inspection target location 9. Beam deflectors for the electron beam 55 are arranged for the purpose of varying the impact location of the electron beam 11 on the sample 5 and for example to perform a raster sweep over an area of the sample surface and to detect particles, in this case secondary electrons, which are generated or set free by the incident beam in order to obtain, using the detector 53, an electron microscope image of the sample 5 in the raster-swept area at the inspection target location 9. As an alternative or in addition, one could also detect other phenomena produced by interaction, such as for example backscattered primary electrons, using suitable detectors. Besides the detector 53 which is arranged within the electron beam column 7 one could arrange, in addition to or instead of the latter, for example one or more secondary particle detectors such as, e.g., an electron detector 57 or an ion detector adjacent to the column 7 inside a first vacuum chamber 59 near the inspection target location 9, likewise for the purpose of detecting secondary particles.

The ion beam column 41 includes an ion source 61 and electrodes 63 serving to produce and accelerate the ion beam 43, as well as beam deflectors 65 for the ion beam and focusing coils or focusing electrodes 67, likewise for the purpose of focusing the ion beam 43 at the inspection target location 9 and to perform a raster sweep over an area of the sample 5.

A gas delivery system 69 includes a reservoir 71 for a process gas which can be brought to the sample by way of a control valve 75 and a conduit 73 which ends near the inspection target location. The process gas can be activated by the ion beam or the electron beam in order to ablate material from the sample 5 or to deposit material on it. The progress of this work process can be observed using the electron beam column 7 and an operatively connected detector 53, 57. An ablation of material can also be achieved through the action of the ion beam alone, without the use of process gas.

The first vacuum chamber 59 is delimited by a chamber wall 79 which includes a first vacuum port 81 connected to a vacuum pump and an air inlet port 83 to vent the chamber. In order to permanently maintain a sufficient vacuum at the electron source 45, even while process gas is delivered into the first vacuum chamber 59, the electron beam column 7 includes a pressure throttle diaphragm 84 and a second pump connector port 85 serving to evacuate the area of the electron source with a separate vacuum pump.

The machining system 1 further includes a laser system 91 configured to direct a laser beam 93 at a second processing target location 95. For this purpose, the laser system 91 is equipped with a laser 97 and a collimator-optics arrangement 99 in order to form the laser beam 93. The laser beam 93 is directed by way of one or more mirrors 101 or by way of light conductors to a location near the chamber wall where the beam falls on a swivel-mounted deflection mirror 103 which directs the beam to the laser-machining target location 95 and which is capable of swiveling as indicated by the arrow 105, so that the laser beam 93 can perform a raster sweep over an area of a sample that is arranged at the laser-machining target location 95.

Along its path, the laser beam 93 enters through an entry window 107 into a vacuum chamber 109 of the laser system, which is likewise delimited by the chamber wall 79, but is separable from the first vacuum chamber 59 by a door 111 which can be opened. FIG. 4 shows a closure panel 113 of the door 111 in the open state indicated by a solid line, while the closed state of the door 111 is indicated by a broken line. An actuator rod 114 of the door serves to move the closure panel 113 in order to switch the door from the open state to the closed state. The door 111 can be configured as a vacuum barrier, being sealed against the chamber wall 79 in order to maintain different vacuum pressures in the first vacuum chamber 59 and in the vacuum chamber 109 of the laser system. In this arrangement, the vacuum chamber 109 of the laser system can be evacuated by way of a pump connector port 115 of the laser system, and vented by way of an air inlet port 116 of the laser system.

Using a transport device 121, the sample 5 can be transported back and forth between the inspection target location 9 and the laser-machining target location 95. To perform this function, the transport device 121 includes a rod 123 which enters through a vacuum-sealed passage 125 into the vacuum compartment 109. Accordingly, the vacuum-sealed passage 125 is arranged closer to the laser-machining target location 95 than to the inspection target location 9. One end of the rod 123 has a coupler 127 which is connected to the base 19 of the positioning table 17.

In the position in which the positioning table 17 is shown in FIG. 4, the sample 5 is located at the inspection target location 9 to undergo inspection or machining with the electron beam 11 or the ion beam 43. In the position indicated by the broken outline, the sample 5 is located at the laser-machining target location 95 to undergo machining with the laser beam 93. Using the transport device 21, the positioning table 17 together with the sample 5 can be moved back and forth between these two positions. To perform this function, the transport device 121 includes a track 131 to support the weight of the positioning table 17 while the latter is being transported and while it is at rest in the laser-machining target location 95. When the table is in its position at the inspection target location 9, the table is supported by the carrier 27 of the sample holder 3.

In the representation shown in FIG. 4, the carrier 27 and the track 131 are separated by a gap 133 in order to allow the carrier 27 to swivel about an axis in a swivel movement perpendicular to the drawing plane without colliding with the track 131, after the rod 123 has been released from the coupler 127 and pulled back slightly (i.e. to the left in FIG. 4). However, it is also possible to pull the base 19 of the positioning device 17 across the gap onto the track 131. The track 131 further has an interruption 135 left free for the panel 111 when the door 111 is in its closed position. The door 111 can be closed after the transport device 123 has pulled the positioning device 17 into the position at the laser-machining target location 95, or if the rod 123 alone has been pulled completely back to the left (in FIG. 4) while the positioning device remains in the position at the inspection target location 9.

At the laser-machining target location 95, the machining of the sample 5 with the laser beam 93 takes place, a process that is accompanied by a deterioration of the vacuum inside the vacuum chamber 109 of the laser system due to particles evaporating or breaking free from the sample 5. In this situation, the closed door 111 prevents a deterioration of the vacuum inside the first vacuum chamber 59 as well as a lasting contamination of the first vacuum chamber 59. Consequently, the electron beam column 7 and the ion beam column 41, among other components, are protected.

The machining of the sample 5 using the laser beam 93 is monitored by an endpoint-detection device 141 which includes for example a light source 143 serving to generate a light beam 144, and a light detector 145. The light beam 144 enters through a first window 146 into the vacuum chamber 109 of the laser system and is directed at the laser-machining target location 95. The light detector 145 receives a light beam 147 which is reflected back from the laser-machining target location 95 through a second window. 148. By analyzing the light received by the light detector 145, it is possible to draw conclusions about the condition of the sample 5 which is being machined with the laser beam 93. In particular, the machining can also be terminated. After the machining with the laser beam has been finished, the door 111 is opened and the sample 5 together with the positioning table 17 is transported by the transport device 121 to the inspection target location 9 where a further machining of the sample 5 with the ion beam 43 and injection of a process gas takes place which can be observed using the electron beam column 7 with the operatively connected detector 53, 57.

FIG. 5 schematically illustrates a system 4 that includes a machining system 1, a controller 2 and a memory 3.

LIST OF REFERENCE SYMBOLS

- 1 machining system
- 5 sample
- 7 electron beam column
- 9 inspection target location
- 11 electron beam
- 17 positioning table
- 19 base
- 21 transport device
- 27 carrier
- 41 ion beam column
- 43 ion beam
- 45 electron source
- 47 cathode
- 49' suppressor electrode
- 49" extractor electrode
- 49''' anode
- 51 condenser lens system
- 53 detector
- 54 objective lens
- 55 beam deflector of the electron beam
- 57 electron detector
- 59 first vacuum chamber
- 61 ion source
- 63 electrodes
- 65 beam deflector of the ion beam
- 67 focussing electrodes
- 69 gas delivery system
- 71 reservoir
- 73 conduit
- 75 valve
- 79 chamber wall
- 81 first pump connector port
- 83 air inlet port
- 84 pressure throttle diaphragm
- 85 second pump connector port
- 91 laser system
- 93 laser beam
- 95 laser-machining target location
- 97 laser
- 99 collimator optics arrangement
- 101 mirror
- 103 swivel-mounted deflection mirror
- 105 arrow
- 107 entry window
- 109 vacuum chamber of the laser system
- 111 door
- 113 closure panel
- 114 actuator rod
- 115 pump connector port of the laser system
- 116 air inlet port
- 121 transport device
- 123 rod
- 125 vacuum-sealed passage
- 127 coupler
- 131 track
- 133 gap
- 135 interruption
- 141 endpoint detection device
- 143 light source
- 144 light beam
- 145 light detector
- 146 first window
- 147 reflected light beam
- 148 second window
- 201 step: inspecting the object
- 202 step: delineating the zone to be investigated
- 203 step: delineating the laser-machining path
- 204 step: removing the material volume along the laser-machining path
- 205 step: inspecting the prepared sample
- 301 object 301a object
301b object
301c object
301d object
302 target structure
303 first boundary demarcation
304 second boundary demarcation
305 base surface of the volume body to be cleared away
306 ablation depth
307 volume to be cleared away
308 TEM lamella
309 FIB/SEM tomography sample
310 EBSD sample
311 X-ray-/synchrotron tomography sample
312 bending beam

What is claimed is:

1. A method, comprising:
   a) determining a path of an object to be processed based on an image of the object so that a sample can be prepared from the object, the image being taken while the object is in a first process chamber using a scanning electron microscope or a focused ion beam; and
   b) after a), while the object is in a second process chamber which is different from the first process chamber, exposing the path to laser light pulses to ablate a volume from the object, the volume being greater than 100 µm³ to provide the sample; and
   c) after b), transferring the sample from the second process chamber to the first process chamber,
   wherein determining the path comprises determining an inner boundary of the path which surrounds the sample and an outer boundary of the path which surrounds the inner boundary of the path so that the ablated volume of the object does not remove the sample from the object.

2. The method of claim 1, further comprising, after c):
   while the object is in the first process chamber, inspecting the sample with the scanning electron microscope or the focused ion beam.

3. The method of claim 1, wherein the object is not observed while being exposed to the laser light pulses.

4. The method of claim 1, further comprising, after c):
   while the object is in the first process chamber, inspecting surface areas of the sample produced by the laser light pulses using the focused ion beam.

5. The method of claim 1, wherein ablating the volume produces a sample for in-situ investigation of micromechanical material properties.

6. The method of claim 1, comprising using a pulse laser to provide the pulses of laser light.

7. The method of claim 1, wherein ablating the volume produces a transmission electron microscopy lamella.

8. The method of claim 1, wherein ablating the volume produces a sample for investigation by focused ion beam/scanning electron microscope-tomography.

9. The method of claim 1, wherein ablating the volume produces a sample for investigation by focused ion beam/scanning electron microscope-tomography, and the method further comprises using the sample in an energy-dispersive X-ray spectroscopy analysis and/or wavelength-dispersive X-ray spectroscopy analysis.

10. The method of claim 1, wherein ablating the volume produces a sample for investigation by electron backscatter diffraction analysis.

11. The method of claim 1, wherein ablating the volume produces a sample for investigation by high-resolution X-ray tomography with an X-ray source.

12. The method of claim 1, wherein ablating the volume produces a sample for investigation by synchrotron tomography.

13. The method of claim 1, further comprising making an undercut to remove the sample from the object, the undercut being made using a laser beam, a focused ion beam or an electron beam.

14. A method, comprising:
   determining a path of an object to be processed based on an image of the object so that a sample can be prepared from the object, the image being determined using a scanning electron microscope or a focused ion beam, the image of the object being taken while the object is in a first process chamber;
   after determining the path, determining a size of a volume to be removed from the object; and
   based on the determined size of the volume to be removed from the object, performing one of the following in a second process chamber which is different from the first process chamber:
      exposing the path to laser light pulses to ablate the volume from the object if the volume being greater than 100 µm³ to provide the sample; or
      exposing the path to a focused ion beam to remove the volume from the object if the volume being less than 100 µm³ to provide the sample.

15. The method of claim 14, wherein determining the path comprises determining an inner boundary of the path which surrounds the sample and an outer boundary of the path which surrounds the inner boundary of the path so that the ablated volume of the object does not remove the sample from the object.

16. An apparatus, comprising:
   a first process chamber comprising an ion microscope configured to provide a focused ion beam and/or a scanning electron microscope;
   a second process chamber comprising a laser system configured to perform laser-machining, the second process chamber being different from the first process chamber; and
   a device configured to transfer the object between the first and second process chambers,
   wherein:
      the apparatus is configured to:
         record an image of an object when the object is in the first process chamber;
         determine a path based on the image;
         prepare a sample out of the object while the object is in the second process chamber via laser-machining to ablate a volume of the object along the path, the ablated volume of the object being 100 µm³ or greater;
         transfer the sample from the second process chamber to the first process chamber to subsequently inspect the sample with the scanning electron microscope and/or the focused ion beam; and
         determine the path by determining an inner boundary of the path which surrounds the sample and an outer boundary of the path which surrounds the inner boundary of the path so that the ablated volume of the object does not remove the sample from the object.

17. The apparatus of claim 16, wherein the laser system comprises a pulse laser configured to perform the laser-machining of the object using light pulses.

18. A method of using an apparatus to prepare a sample from an object, the apparatus comprising a first process chamber and a second process chamber which is different from the first process chamber, the method comprising:

while the object is in the first process chamber, inspecting the object using a scanning electron microscope and/or a focused ion beam to provide an image of the object;

based on the image of the object, delineating a first area of the object which includes the sample to be prepared;

based on the delineated first area of the object, determining a second area of the object which is larger than the first area of the object such that the first area of the object lies completely inside the second area of the object;

while the object is in the second process chamber, using laser-machining to remove a portion of the second area of the object that does not include the first area of the object to provide the sample, the removed portion of the second area of the object having a volume of at least the volume being greater than 100 $\mu m^3$;

moving the sample from the second process chamber to the first process chamber; and while the sample is in the first process chamber, inspecting the sample with the scanning electron microscope and/or the focused ion beam.

19. The method of claim 18, further comprising, after inspecting the sample, polishing the sample with the sample with the scanning electron microscope and/or the focused ion beam.

20. The method of claim 18, wherein ablating the volume produces a transmission electron microscopy lamella.

21. The method of claim 18, wherein the object is not observed while being exposed to the laser light pulses.

* * * * *

UNITED STATES PATENT AND TRADEMARK OFFICE
CERTIFICATE OF CORRECTION

PATENT NO.        : 9,816,946 B2
APPLICATION NO.   : 13/765022
DATED             : November 14, 2017
INVENTOR(S)       : Heiko Stegmann It is certified that error appears in the above-identified patent and that said Letters Patent is hereby corrected as shown below:

In the Claims

Column 17, Lines 25-26, delete "the sample with the sample with the scanning electron microscope" and insert -- the sample with the scanning electron microscope --.

Signed and Sealed this
Thirteenth Day of March, 2018

Andrei Iancu
*Director of the United States Patent and Trademark Office*